United States Patent [19]

Crossley et al.

[11] Patent Number: 5,604,238
[45] Date of Patent: Feb. 18, 1997

[54] Z-BENZYLIDENE-TETRAHYDROQUINOLINES AND ANALOGUES THEREOF

[75] Inventors: Roger Crossley, Woodley; Albert Opalko, Maidenhead, both of England

[73] Assignee: John Wyeth & Brothers Limited, United Kingdom

[21] Appl. No.: 424,690

[22] Filed: Apr. 18, 1995

Related U.S. Application Data

[62] Division of Ser. No. 347,758, Dec. 1, 1994, Pat. No. 5,597,834.

[30] Foreign Application Priority Data

Dec. 1, 1993 [GB] United Kingdom .................. 9324653

[51] Int. Cl.⁶ .................... A61K 31/47; C07D 215/16
[52] U.S. Cl. ............................ 514/299; 546/112
[58] Field of Search ............................. 546/112; 514/299

[56] References Cited

U.S. PATENT DOCUMENTS

| | | | |
|---|---|---|---|
| 4,576,949 | 3/1986 | Smith | 514/277 |
| 4,837,329 | 6/1989 | Crossley | 546/181 |
| 5,001,131 | 3/1991 | Crossley | 514/299 |
| 5,112,832 | 5/1992 | Crossley | 514/299 |

FOREIGN PATENT DOCUMENTS

| | | |
|---|---|---|
| 0161867 | 11/1985 | European Pat. Off. . |
| 2138812 | 10/1984 | United Kingdom . |
| 2138812 | 2/1987 | United Kingdom . |

OTHER PUBLICATIONS

Baum, Chem Ber, vol. 121, pp. 411–415, 1988.
Thummel, J Org Chem. vol. 49, pp. 2208–2212, 1984.
Dammertz, Arch Pharm, vol. 313, pp. 826–832, 1980.

Primary Examiner—C. Warren Ivy
Assistant Examiner—D. Margaret M. Mach
Attorney, Agent, or Firm—R. F. Boswell, Jr.

[57] ABSTRACT

This invention concerns compounds having the Z-configuration of formula:

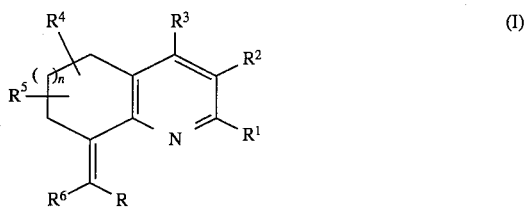

(I)

or salts thereof, wherein R represents an optionally substituted aryl or heteroaryl radical, $R^1$, $R^2$ and $R^3$ each independently represent hydrogen, $C_1$–$C_6$ alkyl, $C_1$–$C_6$ alkoxy, ($C_1$–$C_6$ alkoxy)carbonyl, carboxy, hydroxy ($C_1$–$C_6$)alkyl, halogen, halo($C_1$–$C_6$)alkyl, carboxy($C_1$–$C_6$)alkyl, optionally substituted aryl or heteroaryl or optionally substituted aralkyl or heteroarylalkyl; n represents 0, 1 or 2; $R^4$ and $R^5$ each independently represent hydrogen or a substituent selected from lower alkyl, optionally substituted aryl and optionally substituted aralkyl or $R^4$ and $R^5$ are geminal $C_1$–$C_6$ alkyl substituents and $R^6$ is hydrogen or $C_1$–$C_6$ alkyl which possess antiinflammatory activity.

3 Claims, No Drawings

Z-BENZYLIDENE-TETRAHYDROQUINOLINES AND ANALOGUES THEREOF

This is a division of application Ser. No. 08/347,758, filed Dec. 1, 1994, now U.S. Pat. No. 5,597,834.

This invention relates to heterocyclic compounds, more particularly to 5,6,7,8-tetrahydroquinolines, processes for their preparation and pharmaceutical compositions containing them.

8-Benzylidene-5,6,7,8-tetrahydroquinolines having the E-configuration have been described in the literature—see for example Chemical Abstracts, Volume 73, 87755d and Arch. Pharm. (Weinheim), 1980, 313, pps 826–832 by E. Reimann and co-workers. However no pharmaceutical activity is disclosed.

8-Benzylidene-5,6,7,8-tetrahydroquinolines having utility as inhibitors of the synthesis of leukotrienes and of the action of lipoxygenase in mammals are disclosed in EP-A-0161867. The procedures described in EP-A-0161867 prepare only the E-isomers. U.S. Pat. No. 4,837,329 discloses a broad class of 8-alkylidene-5,6,7,8-tetrahydroquinolines and analogues thereof as intermediates to anti-ulcer compounds.

8-Benzylidene-5,6,7,8-tetrahydroquinolines having the E-configuration which possess anti-ulcer activity are disclosed in our GB Patent Specification No 2138812B.

We have now found a class of 8-benzylidene-5,6,7,8-tetrahydroquinolines having the Z-configuration which possess antiinflammatory activity.

Accordingly this invention provides compounds having the Z-configuration of formula:

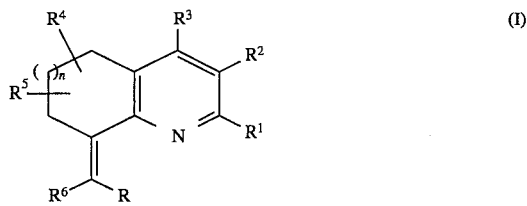

(I)

or a salt thereof, wherein R represents an optionally substituted aryl or heteroaryl radical, $R^1$, $R^2$ and $R^3$ each independently represent hydrogen, $C_1$–$C_6$ alkyl, $C_1$–$C_6$ alkoxy, ($C_1$–$C_6$alkoxy)carbonyl, carboxy, hydroxy($C_1$–$C_6$)alkyl, halogen, halo($C_1$–$C_6$)alkyl, carboxy($C_1$–$C_6$)alkyl, optionally substituted aryl or heteroaryl or optionally substituted aralkyl or heteroarylalkyl;

n represents 0, 1 or 2;

$R^4$ and $R^5$ each independently represent hydrogen or a substituent selected from lower alkyl, optionally substituted aryl and optionally substituted aralkyl or $R^4$ and $R^5$ are geminal $C_1$–$C_6$ alkyl substituents and $R^6$ is hydrogen or $C_1$–$C_6$ alkyl.

In a further aspect this invention provides a Z-isomer of formula I substantially in excess of the corresponding E-isomer, preferably substantially free from the E-isomer, most preferably in at least 98% purity.

By the terms "aryl" or "ar-" as used herein as a group or part of a group, e.g aralkyl, aryloxy, is meant any monovalent carbocyclic radical possessing aromatic character and includes groups having 6 to 10 carbon atoms such as phenyl and naphthyl. By the term "heteroaryl" as used herein as a group or part of a group is meant any monovalent heterocyclic group possessing aromatic character and includes groups having 5 to 10 ring atoms and one or more (e.g 2 or 3) heteroatoms selected from oxygen, nitrogen and sulphur. Examples of heteroaryl radicals are furyl, thienyl, pyrrolyl, pyridinyl, pyrimidinyl, quinolyl, isoquinolyl, benzimidazolyl, thiazolyl and imidazolyl.

The terms "alkyl" or "alk" when used to signify a group or part of a group such as alkoxy, hydroxyalkyl or aralkyl mean any straight or branched saturated aliphatic hydrocarbon having 1 to 6 carbon atoms, e.g 1–4 carbon atoms. Examples are methyl, ethyl, n-propyl, isopropyl, n-butyl, n-pentyl and n-hexyl, each substituted as required.

By the term "optionally substituted" is meant optional substitution on carbon atoms by one or more substituents, e.g substituents commonly used in pharmaceutical chemistry, such as halogen (e.g Cl, Br, F), $C_1$–$C_6$ alkyl, $C_1$–$C_6$ alkoxy, halo($C_1$–$C_6$)alkyl (e.g $CF_3$), or halo($C_1$–$C_6$)alkoxy, (e.g $CHF_2O$, $CF_3CH_2O$—), $NO_2$, $NH_2$, CN, $C_1$–$C_6$ alkylamino di-($C_1$–$C_6$alkyl)amino, carboxy, ($C_1$–$C_6$alkoxy)carbonyl, acyl (e.g ($C_1$–$C_6$alkyl)carbonyl, arylcarbonyl, acylamino, eg. ($C_1$–$C_6$alkyl)CONH, aryl, (e.g phenyl) or amino($C_1$–$C_6$)alkyl.

The term "lower" as used herein to qualify a group means such a group contains 1 to 6 carbon atoms.

Examples of the groups $R^1$, $R^2$ and $R^3$ are independently hydrogen, $C_1$–$C_6$ alkyl (e.g methyl, ethyl, n-propyl, isopropyl, n-butyl, n-pentyl and n-hexyl), —COOH, —COO($C_1$–$C_6$)alkyl (e.g COOMe, COOEt), —$CH_2OH$, Br, Cl, $CF_3$, $C_1$–$C_6$ alkoxy such as OMe, OEt, optionally substituted phenyl or optionally substituted benzyl.

A preferred value for n is 1 such that the compounds are 5,6,7,8-tetrahydroquinolines.

Examples of $R^4$ and $R^5$ are hydrogen and one or more substituents selected from methyl, ethyl, phenyl, phenyl substituted by halogen, $C_1$–$C_6$ alkyl or $C_1$–$C_6$ alkoxy, benzyl and benzyl substituted by halogen, lower alkyl or lower alkoxy. An example of multisubstitution on one carbon atom is gem-dimethyl.

Preferred examples for $R^4$ and $R^5$ are independently hydrogen, methyl and ethyl or $R^4$ and $R^5$ are both gem dimethyl at the 7 position.

Examples of R are phenyl, pyridyl (e.g pyrid-4-yl), quinolyl (e.g quinol-4-yl), 1-naphthyl and 2-naphthyl which groups may be substituted as defined herein, for example by one or more substituents selected from $C_1$–$C_6$ alkyl, $C_1$–$C_6$ alkoxy, halogen, halo $C_1$–$C_6$ alkyl, nitro, amino, mono- or di-($C_1$–$C_6$alkyl)amino, cyano, carboxy, ($C_1$–$C_6$alkoxy)carbonyl and ($C_1$–$C_6$alkyl)carbonyl.

In a preferred aspect this invention provides compounds of formula:

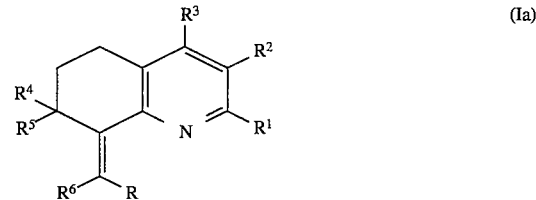

(Ia)

or salts thereof, wherein $R^6$ is H or Me, one of $R^{1-3}$ is $C_1$–$C_6$ alkyl, $CH_2OH$ or COOH, $R^4$ and $R^5$ are each independently hydrogen or methyl and R represents optionally substituted phenyl, pyridyl (e.g pyrid-4-yl) or quinolyl (e.g quinol-4-yl) especially where the substituent is selected from one or more of the following: $C_1$–$C_6$ alkyl, (e.g o-, m- or p- methyl); halogen, (e.g o-, m- or p-chloro or bromo); $C_1$–$C_6$ alkoxy (e.g o-, m- or p-methoxy), and carboxy, (e.g o-, m- or p- carboxy). Other examples include 2,4-dimethylphenyl; 3,4-dimethylphenyl;

4-ethylphenyl; 4-isopropylphenyl, 4-isobutylphenyl, 2-methoxy-4-methylphenyl, 2-chloro-4-methylphenyl.

The compounds of formula I may be obtained in free base form or as acid addition salts as desired. Examples of such salts include salts with pharmaceutically acceptable organic or inorganic acids such as hydrochloric, hydrobromic, hydroiodic, sulphuric, phosphoric, nitric, acetic, citric, tartaric, fumaric, succinic, malonic, formic, maleic acid or organosulphonic acids such as methane sulphonic or p-toluene sulphonic acids.

When acidic substituents are present it is also possible to form salts with bases e.g alkali metals (such as sodium) or ammonium salts. Such salts of the compounds of formula I are included within the scope of this invention.

When basic substituents are present then quaternary ammonium salts may be formed by quaternizing with an alkylating agent such as alkyl or aralkyl halides.

The compounds of formula I possess pharmaceutical acitivity in standard tests, in particular anti-inflammatory activity. In addition we have suprisingly found compounds having the Z- configuration possess potent activity compared with their E- analogues in in vivo tests.

The compounds of formula I were tested for anti-inflammatory activity in the following test procedures:

Rat PMN Assay (Based on Chang, J.; Skowronek, M. D.; Cherney, M. L.; Lewis A. J. Differential effects of putative lipoxygenase inhibitors on arachidonic acid metabolism in cell-free and intact cell preparations. Inflammation 1984, 8, 143–155.)

Glycogen elicited peritoneal cells were collected from female Wistar rats (150–250 g) by lavaging the peritoneal cavity with 50 ml of Hank's balanced salt solution (HBSS) (without $Ca^{++}$ or $Mg^{++}$). Cells were suspended in HBSS ($Mg^{++}$, $Ca^{++}$, 10 mM cystein) such that the cell concentration=$10^7$/ml. One ml aliquots of cells were then incubated with drug (delivered in 10 µl dimethyl sulfoxide (DMSO) for ten minutes in a 37° C. shaking water bath. Samples then received 2.0 µCi [3H]arachidonic acid (AA), 1 µM AA and 1 µM A23187 (delivered in a total of 20 µl DMSO) and were incubated for 10 min in a 37° C. shaking water bath. The reaction was stoped by centrifugation (500×g, 10 min, 4° C.) and the supernatant was directly analysed for eicosanoid content using an HPLC system equipped with an on-line radioactivity detector. Drug effects are determined by comparing integrated dpm/eicosanoid peak values of drug-treated cells to the control (DMSO-treated) cells.

Assessment of Acute Anti-inflammatory Activity Using Rat Carrageenan Edema (Based on Winter, C. A.; Risley E. A.; Nuss, G. W. Carrageenin-Induced Edema in Hind Paw of the Rat as an Assay for Anti-inflammatory drugs. Proc. Soc. Exp. Bil. Med. 1962, 111, 544–7).

Groups of six male Sprague-Dawley rats (Charles River), weighing between 150–165 g. were used in these experiments. Drugs were administered p.o. in 0.5% methylcellulose (400 centipoise). One hour after administering drugs or vehicle, 0.1 ml of 1% carrageenan was injected subplantar into the right hind paw. Right hind paw volumes (ml) were measured prior to carrageenan injection using an automated mercury plethysmograph (i.e zero time reading). After 3 hour post-carrageenan treatment, the right hind paw volumes were remeasured and paw edema was calculated for each rat by subtracting the zero time reading from the 3 hour reading and the percent change in paw edema was calculated. (The Dunnett's test was used to determine statistical significance $P \leq 0.05$).

Rat Adjuvant Arthritis (Developing and Established Model)

(Based on Carlson, R. P.; Datko, L. J.; Chang J.; Nielson, S. T.; Lewis A. J. The anti-inflammatory profile of (5H-dibenzo[A,D]-cyclohepten-5-ylidene)acetic acid (Wy-41, 770), an agent possessing weak prostaglandin synthetase inhibitory activity that is devoid of gastric side effects. Agents and Actions, 1984, 14, 654–661).

Groups of 10 male Lewis rats (Charles River), weighing between 150–170 g., were injected s.c into the right hind paw with desiccated *Mycobacterium butyricum* (0.5 mg/0.1 ml) suspended in light mineral oil. Drugs were administered orally in 0.5% methylcellulose. The following dosing regimens were used; from day 0 to 15 except for weekends (developing model) and days 16 to 29 (established model). Both hind paw volumes (ml) were measured by an automated mercury plethysmography at the time of injection of adjuvant (day 0). Later, paw volumes were measured at day 16, 23, 30 and 44 (uninjected paw) to determine the immunologically-induced (T-cell mediated) inflammation. Drug effects were expressed as a percentage change from vehicle-treated arthritic controls. (The Dunnett's test was used to determine statistical significance $P \leq 0.05$).

Yeast-induced Fever in Rats (Based on Carlson, R. P.; Datko, L. J.; Chang J.; Nielson, S. T.; Lewis A. J. The anti-inflammatory profile of (5H-dibenzo[A,D]-cyhclohepten-5-ylidene)acetic acid (Wy-41, 770), an agent possessing weak prostaglandin synthetase inhibitory activity that is devoid of gastric side effects. Agents and Actions. 1984, 14, 654–661).

Male Sprague-Dawley rats (Charles River), weighing 180–200 g were injected s.c with 2 ml of 7.5% suspension of brewer's yeast in 0.5% methylcellulose. Rectal temperatures were recorded 18 hours later. Rats delveloping a satisfactory pyrexia (viz. a 1.5°–2° C. increase over non-fevered control animals) were divided into groups of six. Drugs were administered orally in 0.5% methylcellulose immediately thereafter, and the mean rectal temperatures were then recorded at 0.5, 1.0, 1.5, and 2 hours. A temperature index was calculated for each rat as the sum of the decreases in temperature (°C.) for each of the readings after drug administration. (The Dunnett's test was used to determine statistical significance $P \leq 0.05$).

The following results were obtained:

TABLE 1

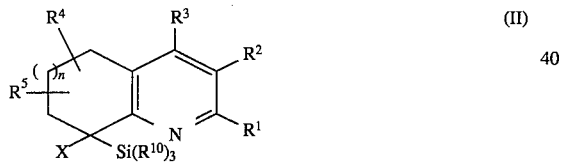

| | | | | | | Rat PMN[d] | | | | Rat | |
| | | | | | | 5-LO | | CO | | Car | Dev |
| Compound | R³ | R² | R⁹ | R⁸ | R⁷ | LTB₄ | 5-HETE | TXB₂ | PGE₂ | Edema[e] | AA[f] |
|---|---|---|---|---|---|---|---|---|---|---|---|
| | Me | H | H | Me | 4-MeC₆H₄ | −18 | +1 | 57 | −49 | −15 | 0 |
| Example 1 | Me | H | H | 4-MeC₆H₄ | Me | −22 | +7 | −22 | +7 | −15 | −14 |
| Example 2 | Me | H | H | 4-Pyridyl | H | −25 | −17 | −87 | +191 | −7 | −49[h] |
| | Me | H | H | H | 4-Pyridyl | −4 | +9 | −75 | +142 | −1 | +3 |
| Example 3 | H | Me | Me | 4-MeC₆H₄ | H | +86 | +97− | −66 | −56 | −48[h] | +8 |
| Example 4 | Me | H | H | 4-Quinolyl | H | −23 | −5 | −18 | −15 | −36[h]− | −38[h] |

[d]Rat Polymorphonuclear leucocyte assay, % change at 10 μM
[e]Rat carrageenan edema assay, % change at 50 mg/kg p.o (3 hr edema)
[f]Rat adjuvant arthritis (developing model) assay, % change at 30 mg/kg, p.o (uninjected paw at day 16)
[h]P ≦ 0.05 from control The results in the Table above show that in the more important in vivo tests (rat carrageenan edema and developing adjuvant arthritis) the compounds with the Z-configuration have good activity in one or both tests.

This invention also provides processes for preparing the compounds of formula I or acid addition salts thereof.

Accordingly this invention provides a process for preparing a compound of formula I which comprises a) reacting a compound of formula II

wherein $R^1$, $R^2$, $R^3$, $R^4$ and $R^5$ are as defined above, $(R^{10})_3$ is defined as three $R^{10}$ radicals the same or different selected from alkyl, cycloalkyl, aralkyl, aryl or electron donating substituents such as alkoxy, cycloalkoxy, aralkoxy, aryloxy, alkylthio, cycloalkythio, aralkylthio or arylthio, the group $R^bR^cN-$ where $R^b$ and $R^c$ are selected from alkyl, cycloalkyl, aryl and aralkyl or $R^b$ and $R^c$ are joined to form a heterocyclic ring with the nitrogen atom to which they are attached (e.g. piperidinyl, pyrrolidinyl which may be substituted e.g by alkyl) and X is sodium, potassium or lithium, with a compound of formula III

RCHO  (III)

wherein R is as defined above in connection with formula I; followed by treatment under acidic or basic conditions and if required removing any protecting groups; or b) dehydrating an alcohol of formula IV

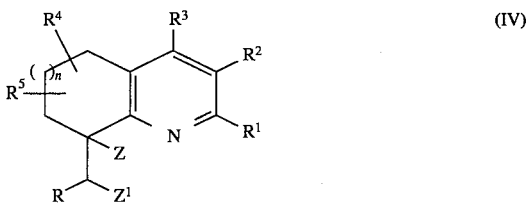

wherein R and $R^{1-5}$ are as defined above; and one of Z and $Z^1$ is OH the other is hydrogen, c) reacting a compound of formula:

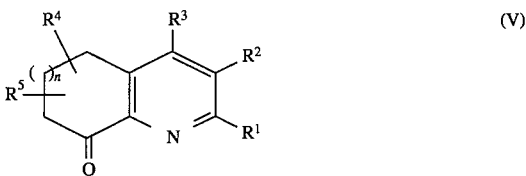

wherein n and $R^{1-5}$ are as defined above, with a compound of formula

where R, $R^{10}$ and X are as defined above, followed by treatment under acidic or basic conditions and if required removing any protecting groups, d) converting a compound of formula I having at least one reactive substituent group to give a different compound of formula I; or e) converting a compound of formula I to an acid addition salt or vice versa.

In process (a) a silicon compound of formula II where $R^1$, $R^2$, $R^3$, $R^4$, $R^5$ and $R^8$ are as previously defined and X is sodium, potassium or lithium is reacted with an aldehyde compound of formula III as hereinbefore defined to obtain a silyl intermediate of formula VII

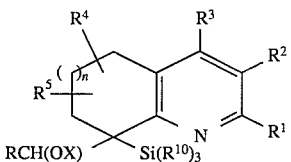

which is converted in situ to compound I by acid or base treatment and removing any protecting groups are required and isolating the product as a free base or acid addition salt. The starting compound II may be prepared as described in our GB Patent No 2122629B or by analogous methods. Briefly a compound of formula VIII

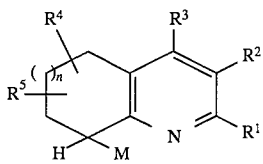

where M is sodium, potassium or lithium is treated with a silylating agent of formula $(R^{10})_3SiHal$ where $R^{10}$ is as defined above and Hal is chlorine, bromine or iodine, to obtain a compound of formula II wherein X is hydrogen and treating this with a metal compound $R*M^2$ where $M^2$ is sodium, potassium or lithium and $R*$ is alkyl, cycloalkyl, aralkyl or aryl or an amine residue to obtain a compound of formula II where X is sodium, potassium or lithium.

The dehydration process (b) is conveniently carried out by treating the compound of formula V with a dehydrating agent such as concentrated sulphuric acid or phosphoric acid. Compounds of formula IV where Z is OH are prepared by reacting a compound of formula V with a Grignard reagent of formula:

$$R\ CH_2\ MG\ hal$$

where hal is chlorine or bromine and R is as defined above. Compounds of formula IV where $Z^1$ is OH are prepared by reacting a compound of formula VIE as defined above with an aldehyde of formula:

$$R\ CHO$$

Process (c) may be conveniently carried out according procedure suitable for process (a). Compounds of formula V and VI are either known in the literature or can be synthesised by analogous methods.

Once a compound of formula I is prepared containing a reactive substituent group, e.g an alkanoyloxy substituent, then such compounds may be converted to a different compound of formula I, e.g hydrolysed to give corresponding hydroxy compounds of formula I. Similarly compounds of formula I containing a hydroxy group may be acylated, e.g using alkanoyl halides to give corresponding alkanoyl compounds of formula I. Similarly when an alkoxy substituent is present then such compounds may be dealkylated using standard procedures to give corresponding hydroxy compounds of formula I. Accordingly compounds of formula I may also be intermediates for other compounds of formula I.

In any of the aforementioned reactions compounds of formula I may be isolated in free base form or as acid addition salts as desired.

This invention also provides pharmaceutical compositions comprising a compound of formula I or a pharmaceutically acceptable salt thereof and a pharmaceutically acceptable carrier.

For the pharmaceutical compositions any suitable carrier known in the art can be used. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or table disintegrating agents; it can also be encapsulating material. In powders the carrier is a finely divided solid which is in admixture with the the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium stearate, talc, sugar, lactose, pectin, dextrin, starch, gelatin, tragacanth, methyl cellulose, sodium carboxymethyl cellulose, a low melting wax and cocoa butter. The term "composition" is intended to include the formulation of an active ingredient with encapsulating material as carrier, to give a capsule in which the active ingredient (with or without other carrier) is surrounded by carriers, which is thus in association with it. Similarly cachets are included.

Sterile liquid form compositions include sterile solutions, suspensions, emulsions, syrups and elixirs.

The active ingredient can be dissolved or suspended in a pharmaceutically acceptable carrier, such a sterile water, sterile organic solvent or a mixture of both. The active ingredients can often be dissolved in a suitable organic solvent, for instance aqueous propylene glycol containing from 10 to 75% of the glycol by weight is generally suitable. Other compositions can be made by dispersing the finely-divided active ingredient in aqueous starch or sodium carboxymethyl cellulose solution, or in a suitable oil, for instance arachis oil. The composition may be administered orally, nasally, rectally or parenterally.

Preferably the pharmaceutical composition is in unit dosage form, the composition is sub-divided in unit doses containing appropriate quantities of the active ingredient; the unit dosage form can be a packaged composition, the package containing specific quantities of compositions, for example packeted powders or vials or ampoules. The unit dosage form can be a capsule, cachet or tablet itself, or it can be the appropriate number of any of these in packaged form. The quantity of active ingredient in a unit dose of composition may be varied or adjusted from 1 to 500 mg or more, e.g 25 mg to 250 mg, according to the particular need and the activity of the active ingredient. The invention also includes the compounds in the absence of carrier where the compounds are in unit dosage form. Based on the results from animal studies the dosage range for the treatment of humans using a compound of formula I will be in the range from about 1 mg to 2 g per day depending on the activity of the compound and the disease to be treated.

For certain of the abovementioned conditions it is clear that the compounds may be used prophylactically as well as for the alleviation of acute symptoms. References herein to "treatment" or the like are to be understood to include such prophylactic treatment, as well as treatment of acute conditions.

The following Examples illustrate the invention and methods for preparing compounds of the invention.

EXAMPLE 1

Z-5,6,7,8-Tetrahydro-4-methyl-8-(1-(4-methyl-phenyl)ethylidene)quinoline 5,6,7,8-Tetrahydro-4-methylquinoline (7.5 g) in tetrahydrofuran (THF) (25 ml) was added to a solution of n-butyl lithium (1.37M, 37 ml) in THF (40 ml) maintained at 0° C. After 30 minutes the solution was blown over with nitrogen onto a solution of trimethylsilyl chloride (5.6 g) in THF (25 ml) at 0° C. Further n-butyl lithium (1.37M, 37 ml) was added and after 30 minutes the reaction mixture was blown over with nitrogen onto 4-methylacetophenone (15 g) in THF (25 ml) at 0° C. After 10 minutes 2M HCl (150 ml) was added.

The aqueous solution was washed with hexane, basified ($Na_2CO_3$) and extracted with dichloromethane. The organic phase was dried ($MgSO_4$) and evaporated under reduced pressure.

The residue (13.2 g) was separated by chromatography on silica using 40% hexane in diisopropylether as eluent. The component with an Rf of 0.23 was collected and the solvent was removed under reduced pressure to give a residue. This residue was purified by chromatography on silica using 40% diisopropylether in hexane as eluent.

The solvent was removed under reduced pressure to give the title compound (2.6 g) mp 89°–93° C.

Analysis: $C_{19}H_{21}N$ requires: C, 86.6; H, 8.0; N, 5.3%, Found: C, 86.8; H, 8.2; N, 5.4%.

EXAMPLE 2

Z-5,6,7,8-Tetrahydro-8-(4-pyridylmethylene)-4-methylquinoline 5,6,7,8-Tetrahydro-4-methylquinoline (2.12 g, 14.4 mmol) in tetrahydrofuran (THF) (10 mL) was added to a solution of n-BuLi (10.6 mL, 1.36M in hexane, 14.4 mmol) in THF (10 mL) maintained at 0° C. After 0.5 hours, this solution was blown over, with $N_2$ onto a solution of trimethylsilyl chloride (1.56 g, 14.4 mmol) in THF (10 mL) at 0° C. Further n-BuLi (10.6 mL, 1.36M in hexane, 14.4 mmol) was added at –5° C. and after 0.5 hours the anion was blown, with $N_2$ onto a solution of 4-pyridinecarboxaldehyde (2.5 g, 23 10 mmol) in THF (10 mL) at 0° C. After 10 minutes 2M HCl (25 mL) was added. The aqueous extract was washed with hexane, then basified ($Na_2CO_3$ solution) and the product extracted into dichloromethane ($CH_2Cl_2$). The $CH_2Cl_2$ layer was dried over $MgSO_4$, then evaporated to give a mixture of E- and Z- isomers. These were separated by chromatography on silica using ethyl acetate (EtOAc) as eluent. The Z-isomer eluted second (Rf 0.08) and collected. Evaporation of the solvent gave a solid which was dissolved in isopropanol (IPA) and treated with ethereal HCl and the solid recrystallised from IPA to give the title compound as the dihydrochloride hydrate. 213°–5° C.; $^1$HNMR (DMSO-$d_6$) δ8.73 (d, J=5 Hz, 2H), 7.74 (d, J=5 H2, 2H), 7.65 (d,=5 Hz, 7.06(s, 1H), 2.92 (t, J=7 Hz, 2H), 2.72 (t, J=7 Hz, 2H), 2.44 (s, 3H), 2.12 (m, 2H).

Analysis: $C_{16}H_{16}N_2.2HCl.H_2O$ requires: C, 58.7; H, 6.2; N, 8.6, Found: C, 58.3; H, 6.0; N, 8.5%.

EXAMPLE 3

Z-5,6,7,8-Tetrahydro-3,7,7-trimethyl-8-(4-methylphenylmethylene)quinoline

R*,S* 1-(4-Methylphenyl)- 1-(5,6,7,8-tetrahydro-3,7,7-trimethylquinol-8-yl)methanol (3.4 g, 11.5 mmol) prepared according to Example 5 of GB Patent Specification 2219797B) in benzene (50 mL) was treated with conc. $H_2SO_4$ (7mL) and stirred at room temperature for 1.25 hours then washed with $Na_2SO_4$ solution (50 mL). The organic phase was separated, washed with water, dried ($MgSO_4$) and evaporated under reduced pressure to give a gum. This was purified by chromatography on silica using $CHCl_3$ as eluent to give an oil (2.7 g). The oil was dissolved in $Et_2O$ and treated with ethereal HCl and evaporated. The yellow gum was triturated with diisopropyl ether to give a yellow solid, which was recrystallised from $Et_2O$ to give 1.4 g (39%) of the title compound as the monohydrochloride: mp 153° C.; $^1$HNMR (DMSO$d_6$) δ8.30 9s, 2H), 7.08 (d,J=8 Hz, 2H), 6.95 (s, 1H), 6.90 (d, J=8 Hz, 2H), 3.02 (t, J=7 Hz, 2H), 2.44 (s, 3H), 2.27 (s, 3H), 1.90 (s, 6H), 1.81 (t, J=7 Hz, 1H).

Analysis: $C_{20}H_{23}N.HCl$ requires: C, 76.7, H, 7.7; N, 4.5, Found: C, 76.6; H, 7.7; N, 4.2%.

EXAMPLE 4

Z-5,6,7,8-Tetrahydro-4-methyl-8-(4-quinolyl-methylene)quinoline 5,6,7,8-Tetrahydro-4-methyl-8-trimethylsilylquinoline (3.81 g) (prepared by reacting 5,6,7,8-tetrahydro-4-methylquinoline, n-butyl lithium and trimethylsilyl chloride) was dissolved in THF (20 ml) at 0° C. and treated with n-butyl lithium (1.57M, 12 ml). The mixture was blown by nitrogen onto a solution of 4-quinolinecarboxaldehyde (5.5 g) in THF (40 ml) and after 10 minutes 2M HCl (35 ml) was added.

The aqueous layer was washed with hexane, basified ($Na_2CO_3$) and extracted into dichloromethane. The aqueous layer was dried ($MgSO_4$) and evaporated under reduced pressure. The residue was purified by chromatography on silica using dichloromethane to elute unreacted 4-quinolinecarboxaldehyde and then with 1:1 methanol/dichloromethane to elute the remaining material.

The solvent was removed under reduced pressure and the residue was purified by chromatography on silica using 5% methanol in chloroform as eluent. Fractions containing material with an Rf. value of 0.43 yielded the E isomer. Fractions containing material with an Rf. value of 0.29 were evaporated under reduced pressure and the residue was recrystallised from cyclohexane to give the title compound as the hemihydrate (0.96 g) mp 91° C.

Analysis: $C_{20}H_{18}N_2.½H_2O$ requires: C, 81.1; H, 6.5; N, 9.5%, Found: C, 81.1; H, 6.7; N, 9.3%.

We claim:

1. A compound having the Z-configuration of formula:

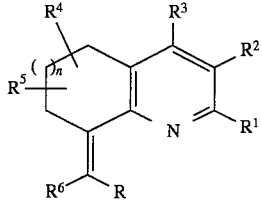

or a salt thereof, wherein n is 2;

R is selected from furyl, thienyl, pyrrolyl, pyridinyl, pyrimidinyl, quinolyl, isoquinolyl, benzimidazolyl, thiazolyl and imidazolyl, optionally substituted by one or more substituents selected from halogen, $C_1-C_6$ alkyl, $C_1-C_6$ alkoxy, halo($C_1-C_6$)alkyl, halo($C_1$-$C_6$)alkoxy, $NO_2$, $NH_2$, CN, $C_1$-$C_6$ alkylamino, carboxy($C_1$-$C_6$ alkoxy)carbonyl, ($C_1$-$C_6$ alkyl)carbonyl, arylcarbonyl, ($C_1$-$C_6$ alkyl)CONH, phenyl or amino($C_1$-$C_6$)alkyl;

$R^1$, $R^2$, and $R^3$ each independently represent hydrogen, $C_1$-$C_6$ alkyl, $C_1$-$C_6$ alkoxy, ($C_1$-$C_6$ alkoxy)carbonyl, carboxy, hydroxy($C_1$-$C_6$)alkyl, halogen, halo($C_1$-$C_6$)alkyl, carboxy($C_1$-$C_6$)alkyl, optionally substituted aryl or heteroaryl or optionally substituted aralkyl or heteroarylalkyl;

$R^4$ and $R^5$ each independently represent hydrogen or a substitutent selected from $C_1$-$C_6$ alkyl, optionally substituted aryl and optionally substituted aralkyl or $R^4$ and $R^5$ are geminal ($C_1$-$C_6$)alkyl substituents; and $R^6$ is hydrogen or $C_1$-$C_6$ alkyl.

2. A pharmaceutical composition comprising a pharmaceutical carrier and a therapeutically effective amount of a compound having the Z-configuration of the formula:

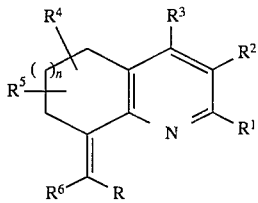

or a salt thereof, wherein n is 2;

R is selected from furyl, thienyl, pyrrolyl, pyridinyl, pyrimidinyl, quinolyl, isoquinolyl, benzimidazolyl, thiazolyl and imidazolyl, optionally substituted by one or more substituents selected from halogen, $C_1$-$C_6$ alkyl, $C_1$-$C_6$ alkoxy, halo($C_1$-$C_6$)alkyl, halo($C_1$-$C_6$)alkoxy, $NO_2$, $NH_2$, CN, $C_1$-$C_6$ alkylamino, carboxy($C_1$-$C_6$ alkoxy)carbonyl, ($C_1$-$C_6$ alkyl)carbonyl, arylcarbonyl, ($C_1$-$C_6$ alkyl)CONH, phenyl or amino($C_1$-$C_6$)alkyl;

$R^1$, $R^2$, and $R^3$ each independently represent hydrogen, $C_1 C_6$ alkyl, $C_1 C_6$ alkoxy, ($C_1 C_6$ alkoxy)carbonyl, carboxy, hydroxy($C_1$-$C_6$)alkyl, halogen, halo($C_1$-$C_6$)alkyl, carboxy($C_1$-$C_6$)alkyl, optionally substituted aryl or heteroaryl or optionally substituted aralkyl or heteroarylalkyl;

$R^4$ and $R^5$ each independently represent hydrogen or a substitutent selected from $C_1$-$C_6$ alkyl, optionally substituted aryl and optionally substituted aralkyl or $R^4$ and $R^5$ are geminal ($C_1$-$C_6$)alkyl substituents; and $R^6$ is hydrogen or $C_1$-$C_6$ alkyl.

3. A compound as claimed in claim 1 which is in the form of an acid addition salt with a pharmaceutically acceptable acid selected from hydrochloric, hydrobromic, hydroiodic, sulphuric, phosphoric, nitric, acetic, citric, tartaric, fumaric, succinic, malonic, formic, maleic acid, methane sulphonic or p-toluene sulphonic acid.

* * * * *